United States Patent [19]

Umezawa, deceased et al.

[11] Patent Number: 4,870,207

[45] Date of Patent: Sep. 26, 1989

[54] SYNTHESIS OF ARPHAMENINE A

[75] Inventors: Hamao Umezawa, deceased, late of Tokyo, by Mieko Umezawa, Kazuo Umezawa, Yoji Umezawa, legal representatives; Takaaki Aoyagi, Kanagawa; Kuniaki Tatsuta, Tokyo; Takeshi Nakamura, Kanagawa; Shunzo Fukatsu, Tokyo, all of Japan

[73] Assignee: Zaiden Hojin Biseibutsu Kagaku Kenkyu Kai, Japan

[21] Appl. No.: 79,319

[22] Filed: Jul. 30, 1987

Related U.S. Application Data

[63] Continuation-in-part of Ser. No. 619,322, Jun. 11, 1984, abandoned.

[30] Foreign Application Priority Data

Jun. 17, 1983 [JP] Japan .................. 58-107888

[51] Int. Cl.$^4$ ............................. C07C 129/12
[52] U.S. Cl. .................. 562/439; 549/415; 560/25
[58] Field of Search ............................ 562/439

[56] References Cited

U.S. PATENT DOCUMENTS 4,281,180  7/1981  Umezawa et al. .......... 562/444 X R
4,584,398  4/1986  Kuroiwa et al. ............. 562/439
4,595,698  6/1986  Umezawa et al. .......... 562/439 X R

FOREIGN PATENT DOCUMENTS 9144717  8/1984  Japan ........................... 562/439

OTHER PUBLICATIONS

House, "Modern Synthetic Reactions", 2nd ed (1972), pp. 510–511, Benjamin/Cummings Pub. Co., Menlo Park, Calif.
Royals, "Advanced Org. Chem." (1954), p. 749; Constable & Co. Ltd. London.
Rodd, "Chemistry of Carbon Compounds", (1951), (Editor), vol. 1, Part A, p. 573, Elsenies Pub. Co., London, N.Y.
McOmie (Editor) "Protective Groups in Org. Chem", 1973, Plenum Press, London & N.Y., pp. 46–47.
Meyer, et al.; J. of Med. Chem., 2y (1981), pp. 964–969.
Jennings-White, et al., Tetrahedron Letters, 23 (1982), pp. 2533–2534.

Primary Examiner—Joseph Paul Brust
Attorney, Agent, or Firm—Larson and Taylor

[57] ABSTRACT

Known compound, optically active arphamenine A can now be synthesized in an optically active pure form and in a favorable yield by a new process comprising consecutive steps with starting from L-arginine, wherein racemization of intermediate reaction products can be minimized.

1 Claim, No Drawings

SYNTHESIS OF ARPHAMENINE A

CROSS-REFERENCE TO RELATED APPLICATION

This application is a continuation-in-part application of U.S. patent application Ser. No. 619,322 filed June 11, 1984, which is now abandoned.

SUMMARY OF THE INVENTION

This invention relates to a process for the productiuon of optically active arphamenine A along with epi-arphamenine A, a new arphamenine-related compound.

BACKGROUND OF THE INVENTION

Arphamenine A may be deemed as an optically active derivative of L-arginine, which is produced fermentatively by a microorganism, *Chromobacterium violaceus* BMG361-CF4 (ATCC 39373). Arphamenine A is the novel substance which was discovered by the present inventors as aminopeptidase-inhibitor and which shows an immunopotentiating activity and an analgesic activity (see Japanese patent application No. 96,276/84; U.S. Pat. No. 4,595,698 and U.S. patent application Ser. No. 809,215).

Arphamenine A is of the chemical structure represented by the following formula

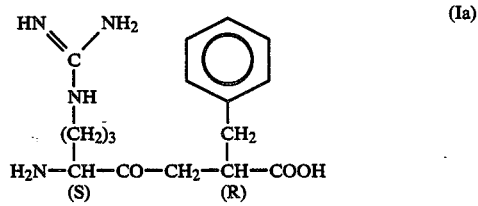

During the inventors' extensive researches in an attempt to synthesize arphamenine A and its related compounds, it has now been found that the arphamenine A can be synthesized in a facile way and in a favorable yield by starting from L-arginine, converting it into an iodomethylketone derivative thereof, and reacting the latter with a metal salt derivative of a benzyl-substituted malonic acid diester. Further, it has now been found that the functional groups present in the necessary reactants, namely L-arginine and the malonic acid derivatives employed must be protected by such protective groups which can readily be cleaved under mild reaction conditions with involving neither the racemization at the α-carbon atom of L-arginine nor the decomposition of the instable guanidino group of L-arginine in the course of carrying out the synthetic process. When an optically active compound of such structure, like the arphamenine A of the formula

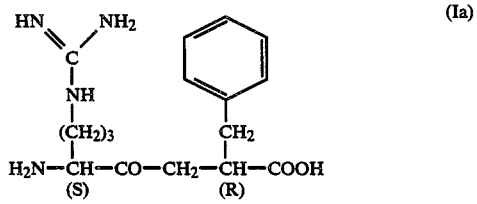

wherein there exist two asymmetrical carbon atoms, the one in the α-amino acid residue moiety and the other in the 2-position adjacent to the terminal carboxyl group, which are linked by a ketomethylene group (CO—CH$_2$—), is to be synthetized frrom an L-α-amino acid, the drawback is likely to occur that racemization would take place at the α-carbon atom of the α-amino acid moiety in the course of the synthetic route, if there is used a method comprising an application of Dakin-West reaction using a ketomethylene compound and oxazolone, followed by hydrolysis under strong acidic conditions (see "Journal of Medicinal Chemistry" Vol. 24, page 964 (1981)), or alternatively a method comprising reacting a Grignard reagent with an ester of an amino acid with pyridine-thiol (see "Tetrahedron Letter" Vol. 23, page 2533 (1982)). Further, the former method using the Dakin-West reaction is disadvantageous not only in that the necessary starting ketomethylene compound, namely a half-ester or half-acid chloride of succinic acid derivative is difficult to prepare, but also in that the intermediate condensation product whose the amino group has been acylated is formed, with the consequence that the deprotection of the N-acyl group in the last stage requires a hydrolysis under strong acidic conditions. Besides, the latter method using the Grignard reaction is also disadvantageous not only in that the starting compound as needed can be chosen only within a limited scope of compound because of the required use of the Grignard reagent, but also in that the reaction procedures involved are troublesome, for example, owing to the need for protection of the ketone group in the starting compound.

An object of this invention is to provide a process of synthesizing arphamenine A, which can be operated in a facile way nd at a higher yield of arphamenine A of a highly pure, optically-active form, than when using the prior art methods as mentioned above. Another objects of this invention will be clear from the following descriptions.

DETAILED DESCRIPTION OF THE INVENTION

According to a first aspect of this invention, therefore, there is provided a process for the production of optically active arphamenine A of the formula (Ia)

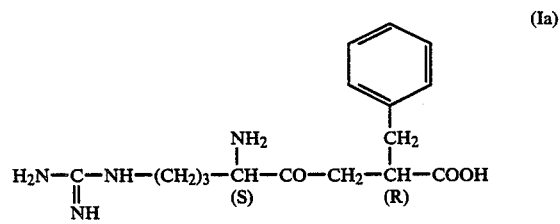

and optically active epi-arphamenine A of the formula (Ib)

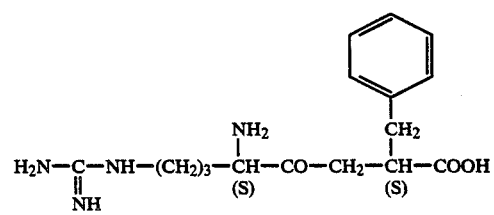

which comprises the consecutive steps of:

(i) reacting an optically active L-arginine amino-protected derivative represented by the formula (V)

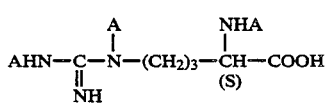

wherein A denotes an amino-protecting group selected from the group consisting of benzyloxycarbonyl, p-nitrobenzyloxycarbonyl and p-methoxybenzyloxycarbonyl, with ethyl chloroformate in an anhydrous organic solvent to form the mixed acid anhydride of the formula (VI)

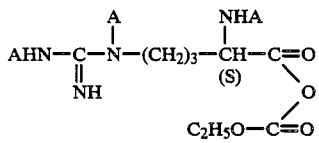

wherein A is as defined above, followed by reacting the latter reaction product of the formula (VI) with diazomethane to produce an optically active diazomethane derivative of the formula (VII)

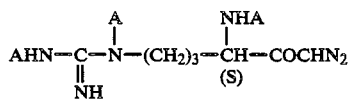

wherein A is as defined above, (ii) reacting the diazomethane derivative of the formula (VII) with hydrobromic acid to form a bromo derivative of the formula (IIa)

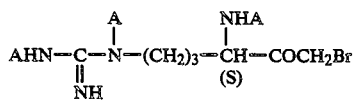

wherein A is as defined above, which is then reacted with sodium iodide to produce an iodo derivative of the formula (IIb)

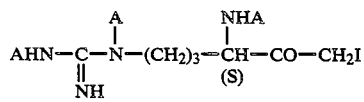

wherein A is as defined above, (iii) condensing the resulting iodo derivative of the formula (IIb) with an alkali metal salt of a benzyl-substituted malonic acid diester of the formula (III)

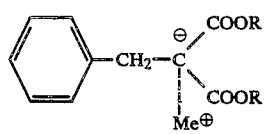

wherein R is a carboxyl-protecting group selected from the group consisting iof tetrahydropyranyl and tert.-butyl; and Me is an alkali metal, at a temperature of 0°–15° C., to produce as the condensation product a dicarboxylic acid compound of the formula (IV)

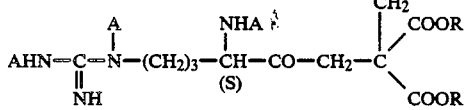

wherein A and R are each as defined above, (iv) hydrolysing the dicarboxylic acid compound of the formula (IV) into the free dicarboxylic acid compound of the formula (IVa)

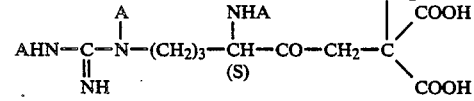

wherein A is as defined above, under such weakly acidic conditions that the asymmetric carbon atom having the S-configration in the compound of the formula (IVa) does not undergo racemization, (v) removing one carboxyl group from the dicarboxylic acid compound (IVa) by heating the latter in an organic solvent in the presence of an alkali metal chloride at a temperature of 100°–130° C., to produce a racemic mixture of monocarboxylic acid compounds of the formula (VIII)

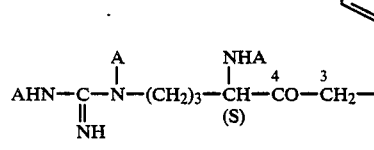

wherein A is as defined above, and (vi) chromatographying the racemic monocarboxylic acid compounds (VIII) into the optically active arphamenine A amino-protected derivative (the 2R-isomer) of the formula (VIIIa)

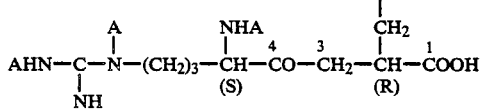

and the optically active epi-arphamenine A amino-protected derivative (the 2S-isomer) of the formula (VIIIb)

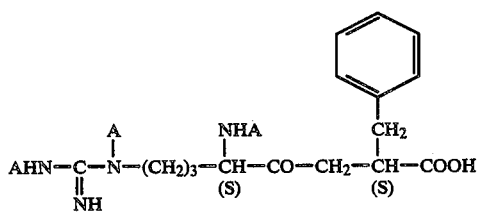

(VIIIb)

wherein A is as defined above, and
(vii) removing the amino-protecting group (A) from the 2R-isomer compound of the formula (VIIIa) and from the 2S-isomer compound of the formula (VIIIb) respectively to produce the optically active arphamenine A (the 2R-isomer) of the formula (Ia)

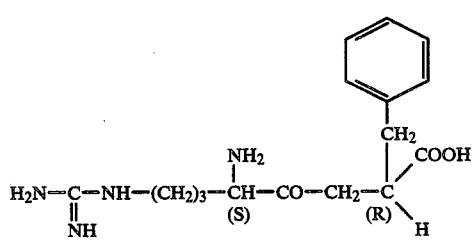

(Ia)

and the optically active epi-arphamenine A (the 2S-isomer) of the formula (Ib)

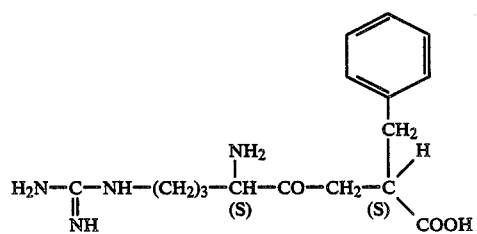

(Ib)

In the process of this invention, the strting L-arginine amino-protected derivative of formula (V) has its amino groups protected by the benzyloxycarbonyl, p-nitrobenzyloxycarbonyl or p-methoxybenzyloxycarbonyl group as the especially selected amino-protecting group, and owing to this, the removal of this amino-protecting group from the intermediate arphamenine A ior epi-arphamenine A compound of formula (VIIIa) or (VIIIb) can be achieved under very much mild reactions conditions, for example, at room temperature under neutral condition, with invoking neither the racemization at the asymmetrical α-carbon atom of the arginine moiety having the (S)-configuration at said α-carbon atom, nor the decomposition of the guanidino group. Besides, the alkali metal salt of the benzyl-substituted malonic acid diester of formula (III) has its carboxyl group each protected by the carboxyl-protecting tetrahydropyranyl or tert-butyl group which is especially very much readily cleavable hydrolytically under very weakly acidic condition, and owing to this, the removal of this particular type of the carboxyl-protecting group from the dicarboxylic acid ester compound of formula (IV) by hydrolysis can easily be performed under very much weakly acidic conditions. Accordingly, the removal of all the protective groups from the intermediate products as formed in the process can be accomplished with involving neither the racemization at said asymmetrical α-carbon atom of the L-arginine moiety nor the decomposition of the instable guanidino group of the L-arginine moiety but with retaining the orginal (S)-configuration at said asymmetrical α-carbon atom, so that the desired arphamenine A can be obtained in a high òptical purity and at a high yield.

In case the amino groups of the starting L-arginine amino-protected derivative of formula (V) would be protected—not in accordance with this invention—by such a conventional amino-protecting group of the acyl type, such as benzoyl and acetyl which is removable only by hydrolysis under somewhat strong acidic conditions, and in case the alkali metal salt of the malonic acid diester of formula (III) would have its carboxyl groups protected by a conventional carboxyl-protecting group such as alkyl group, especially methyl and ethyl, which is removable under basic condition, the removal of these protective groups can be removed only under such strong reaction conditions which should invoke the racemization at the aforesaid asymmetrical α-carbon atom and also the decomposition of said guanidino group, resulting in a remarkably lowered yield of the optically active arphamenine A desired. By virture of the selection of the particular types of the above-mentioned amino-protecting group and the above-mentioned carboxyl-protecting group and the ingenious combination of the steps (i) to (vii) of the present process, the process of this invention can give arphamenine A in a high optical purity and at a high yield.

In the process of this invention, the step (i) of reacting the L-arginine amino-protected derivative of formula (V) with ethyl chloroformate may suitably be carried out in solution in an anhydrous organic solvent such as tetrahydrofuran and diethyl ether in the presence of an amine such as triethylamine as an acid-binding agent at a low temperature in a range of −20° to 0° C. The resulting reaction product of formula (VI) may then be reacted with diazomethane to produce a diazomethane derivative of formula (VII). This reaction may be carried out in an anhydrous organic solvent such as tetrahydrofuran at a low temperature in a range of −20° C. to 10° C.

The above steps for producing the compounds of formulae (VI) and (VII) from the compound of formula (V) may be conducted generally according to the method of Stachowiak et al (see "Journal of Medicinal Chemistry" Vol. 22, page 1127 (1979). Then, the diazomethane derivative of formula (VII) may be reacted in the step (ii) of the present process with hydrobromic acid in acetic acid or in a mixture of acetic acid and diethyl ether at a temperature in a range of −10° C. to 10° C., to produce the bromo derivative of formula (IIa). In a subsequent step, the bromo derivative of formula (IIa) is reacted with sodium iodide in an inert organic solvent such as acetone and methylethylketone, to produce the iodo derivative of formula (IIb).

The malonic acid diester alkali metal salt of the formula (III) which is used as the reactant in the process of this invention can be prepared by reacting a benzyl-substituted malonic acid diester of the general formula (IIIa)

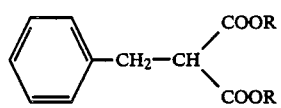

(IIIa)

wherein R is as defined in the above formula (III), with an alkali metal hydride, preferably, sodium hydride, in a liquid mixture of N,N-dimethylformamide and hexamethylphosphoric triamide (HMPA).

In the process of this invention, the condensation of the compound of formula (IIb) with the compound of formula (III) can be achieved, for example, by reacting both these compounds with each other in an ordinary, inert organic solent such as formamide, dimethylformamide or HMPA, for several hours at a temperature of 0° to 15° C. under ice-cooling.

The condensation reaction of the compound of formula (IIb) with the compound of formula (III) gives the dicarboxylic acid ester compound of formula (IV). This compound (IV) is then decarboxylated by removing one carboxyl group-COOR therefrom. It is convenient to effect the decarboxylation of the compound (IV) by converting the dicarboxylate compound (IV) at first into its free dicarboxylic acid compound of formula (IVa) by hydrolysis, under very weakly acidic conditions, and then heating the free dicarboxylic acid (IVa) in an organic solvent such as pyridine or dimethylformamide, in the presence of an alkali metal chloride such as sodium chloride at a temperature of 100° C. to 130° C. for a time of 10–60 minutes, preferably of 10–30 minutes. By this mono-decarboxylation, there is produced a racemic mixture of the monocarboxylic acid compounds of formula (VIII) above, which is composed of the mixture of the 5S,2R-isomer and the 5S,2S-isomer.

The racemic mixture of the compounds (VIII) may be separated into the optically active 5S,2R-isomer of formula (VIIIa), namely the arphamenine A aminoprotected derivative, and into the optically active 5S,2S-isomer of formula (VIIIb), namely the epi-arphamenine A amino-protected derivative, by chromatographying said racemic mixture of the compounds (VIII), for example, in column of silica gel as developed with chloroform-methanol or in a column of other suitable absorbent material.

The compound of formula (VIIIa) and the compound of formula (VIIIb) are then separately deprotected to give the compound of formula (Ia) (arphamenine A) and the compound of formula (b) (epi-arphamenine), respectively. For this deprotection purpose, the benzyloxycarbonyl group may readily be removed at room temperature by catalytic hydrogenolysis in a manner known per se.

The compounds of the formula (Ia) and (Ib) as produced according to the process of this invention, each exhibit an activity inhibitory to aminopeptidase B at its concentration in a range of 0.002 mcg/ml to 50 mcg/ml, and they also exhibit a cell-mediated immunopotentiating activity, similarly to the natural arphamenine A, when tested according to the known Delayed-Type Hypersensitivity (D.T.H.) technique. Accordingly, they are useful as an immunopotentiating agent.

This invention is now illustrated with the following Examples to which this invention is not limited in any way.

EXAMPLE 1

(a) Preparation of tri-N-benzyloxycarbonyl-L-arginyldiazomethane

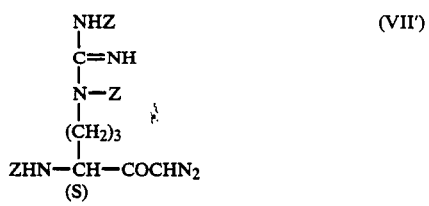

(VII')

where Z denotes benzyloxycarbonyl group: $C_6H_5CH_2OCO-$ here and also hereinafter unless otherwise stated. Tri-N-benzyloxycarbonyl-L-arginine (3.85 g; 6.67 mmols) (a product of kokusan Kagaku, Japan) of the formula

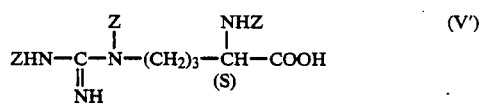

(V')

where Z is benzyloxycarbonyl group, and 0.927 ml (6.67 mmols) of triethylamine were suspended in 50 ml of anhydrous tetrahydrofuran, and the suspension was cooled to −15° C. in a solid carbon dioxide-acetone bath. 0.638 ml (6.67 mmols) of ethyl chloroformate was added dropwise to the suspension in about 5 minutes with stirring and with keeping the reaction temperature at −15° C., to effect the reaction. The resulting reaction mixture was maintained at the same temperature for an additional 15 minutes to produce a compound of formula

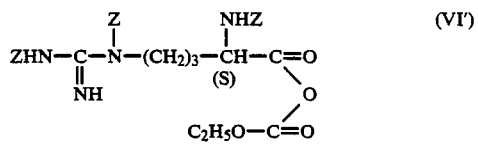

(VI')

where Z is s defined above.

20 ml of an ice-cooled ethereal solution of diazomethane (diazomethane content: about 15 mmols), which had been prepared by a known method from 2 g of N-nitrosomethylurea, was added at once to the above reaction mixture. After the reaction temperature was held in a range of −10° C.±5° C. for about 1 hour, the solvents were evaporated from the resulting reaction solution under reduced pressure.

The residue comprising the reaction product compound of formula (VII') given above was dissolved in 50 ml of ethyl acetate, and the solution was washed with water and with a saturated aqueous sodium bicarbonate. Then, the solution was washed twice with water and dried over anhydrous sodium sulfate. The dried solution was filtered, and the filtrate was concentrated to about 10 ml. Then, petroleum ether was added in such an amount as to make the concentrate cloudy, and deposit crystals. After the mixture was allowed to stand overnight at room temperature, the crystals were collected by filtration and washed with a mixture of ethyl acetate and petroleum ether. 2.498 g (4.32 mols) of the titled compound (VII') was obtained as yellow crystals.

Yield: 65%. m.p.: 117.5°–118.5° C. IR($\nu_{max}^{cm-1}$): 2110, 1720–1700 Mass spectrum (FD): m/e 577 (m+1). Elemental Analysis ($C_{31}H_{32}N_6O_7$). Calcd: C 61.99, H 5.37, N 13.99, O 18.65%. Found: C 61.95, H 5.25, N 13.70, O 18.80%.

(b) Preparation of tri-N-benzyloxycarbonyl-L-arginylbromomethane

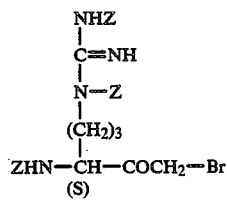
(IIa')

2.450 g (4.08 mmols) of the diazomethane compound of formula (VII') as obtained in the step (a) above was dissolved in 20 ml of tetrahydrofuran, and the solution was cooled with ice. 15 ml of a solution which had been prepared by diluting a solution of 25% hydrobromic acid in acetic acid to a 10-fold volume with ether was added dropwise to said solution of the diazomethane compound (VII') in 3 hours under ice-cooling. The solvents were evaporated from the resulting reaction mixture under reduced pressure.

The resulting residue comprising the compound of formula (IIa') above was dissolved in 50 ml of ethyl acetate. The solution obtained was then washed with water, with a saturated aqueous sodium bicarbonate and finally with water (twice), and dried over anhydrous magnesium sulfate. After filtration, the filtrate was concentrated to about 7 ml for crystallization. The crystals formed were collected by filtration and washed with a mixture of ethyl acetate and petroleum ether. After drying, the captioned compound (IIa') was obtained as colorless needle crystal.

Yield: 80%. m.p.: 136.5°–137° C. Mass spectrum (FD): m/e 655 (m+2), 653 (m). Beilstein's test: Positive. $[\alpha]_{365}^{20} -25°$ (c=0.75, chloroform). Elemental analysis ($C_{31}H_{33}N_4O_7Br$): Calcd: C 56,98, H 5.09, N 8.57, O 17.14, Br 12.22%. Found: C 56.87, H 5.01, N 8.49, O 17.41, Br 12.43%.

(c) Preparation of tri-N-benzyloxycarbonyl-L-arginyliodomethane

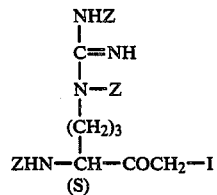
(IIb')

130.7 mg (0.2 mmol) of the bromomethane derivative of formula (IIa') as produced in the step (b), and 90 mg (0.6 mmol) of sodium iodide were suspended in 2 ml of acetone, and the suspension was kept for 3 hours at room temperature in dark for the reaction. Thin-layer chromatography (Merck's silica gel plate Art 5715) of the reaction mixture developed with benzene-acetone (10:1) was made to confirm the disappearance of the starting material and the appearance of a new spot. Then, the solvent was evaporated from the reaction mixture under reduced pressure, and the residue was dissolved in 10 ml of ethyl acetate. The solution was washed with three 7 ml portions of water and dried over anhydrous magnesium sulfate. After filtration, the filtrate was concentrated to about one-third of the original volume. Ether was added to the concentrate for crystallization. 96 mg of the primary crystals of the titled compound (IIb') formed were collected by filtration, and then the filtrate was concentrated, affording 30 mg of the crystals as second crop. Total amount of crystals collected: 126 mg (0.180 mmol).

Yield: 90%. m.p.: 136°–136.5° C. Mass spectrum (FD): m/e 701 (m+1). Beilstein's test: Positive. Elemental analysis ($C_{31}H_{33}N_4O_7I$): Calcd: C 53.14, H 4.75, N 8.00, O 15.99, I 18.12%. Found: C 53.18, H 4.74, N 8.03%.

(d) Preparation of sodium salt of benzylmalonic acid di-tetrahydropyranyl-ester

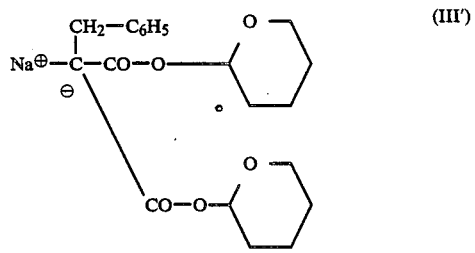
(III')

Benzylmalonic acid di-tetrahydropyranyl-ester of the formula

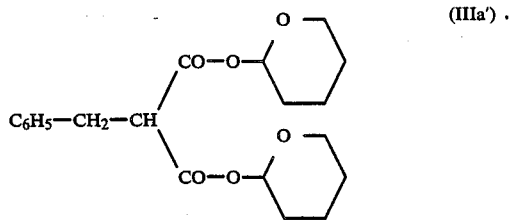
(IIIa')

was first prepared in accordance with the method of Bowman and Fordham ("Journal of Chemical Society", page 3945, 1952) as follows:

0.583 g (3 mmols) of benzylmalonic acid and 1.45 ml (16 mmols) of dihydropyran were reacted with each other in 15 ml of benzene under ice-cooling in the presence of a drop of concentrated sulfuric acid as catalyst. 250 mg of KOH was added to the mixture, and the mixture was stirred for 30 minutes. The supernatant was taken by decantation and distilled under reduced pressure in a water bath kept below 30° C. to remove the benzene therefrom. The desired diester was obtained as colorless oil.

The resulting oil was dissolved in a mixture of 2 ml of N,N-dimethylformamide and 0.5 ml of hexamethylphosphoric triamide (HMPA). The solution obtained was cooled with ice, to which then 36 mg (1.5 mmols) of sodium hydride was added. The mixture was stirred for one hour under ice-cooling to give a clear solution containing the captioned sodium salt of formula (III') above.

EXAMPLE 2

Synthesis of optically active arphamenine A

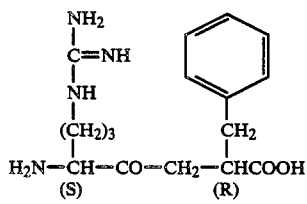

(a) Condensation reaction

To the clear solution containing the sodium salt of benzylmalonic acid di-tetrahydropyranyl-ester having formula (III'), which was prepared in the step (d) of Example 1, was added 701 mg (1 mmol) of the tri-N-benzyloxycarbonyl-L-arginyl-iodomethane of formula (IIb') which was prepared in the step (c) of Example 1. The mixture so obtained was stirred for 2 hours under ice-cooling, and the condensation reaction was allowed to occur. Thin-layer chromatography on silica gel of the reaction mixture was made to confirm disappearance of the starting iodomethane compound (IIb'). In the reaction mixture, there was formed the condensation product of formula

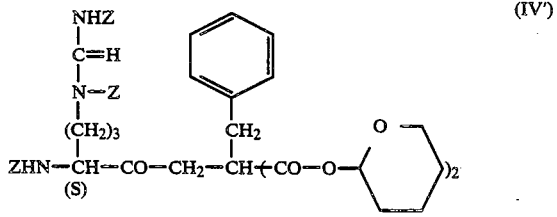

where Z denotes a benzyloxycarbonyl group.

(b) Decarboxylation reaction 5 ml of dioxane was added to the reaction mixture of the above step (a), and 1.5 ml of 1N HCl was further added thereto in 2 minutes under ice-cooling. The resulting mixture was stirred for 3 hours under ice-cooling and then for 2 hours at room temperature to effect hydrolysis of the compound (IV'), when the reaction of cleaving the tetrahydropyranyl group from the condensation product of formula (IV') above took place in the reaction mixture to form a dicarboxylic acid compound of the formula

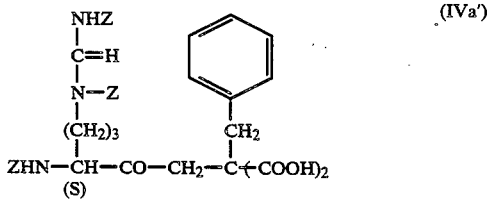

wherein Z is benzyloxycarbonyl group. When a portion was taken as sample out of the hydrolysis reaction mixture as such and concentrated, followed by addition of an ether solution of diazomethane to the concentrated sample in dioxane, there is then formed a dimethyl ester of the compound (IVa') which was found to be conforming to an authentic sample of a separately synthesized product described below, in terms of their NMR spectrum, thin-layer chromatogram, and mass spectrum (FD) (m/e 794).

The hydrolysis reaction mixture was distilled under reduced pressure to remove the dioxane, hydrochloric acid and water therefrom. 5 ml of pyridine was added to the residue, and the mixture was heated to 100° C., when the generation of gases including carbon dioxide was observed by the decarboxylation reaction. Generation of the gases stopped in about 20 minutes, and thin-layer chromatography (Merck's silica gel plate Art 5717, developed with chloroform-methanol-acetic acid=10:1:0.5) of the reaction mixture was made to confirm the disappearance of the dicarboxylic acid (IVa') and the formation of two new spots. The reaction mixture was distilled under reduced pressure to remove the pyridine and N,N-dimethylformamide therefrom. The residue was dissolved in 15 ml of ethyl acetate, and the solution was washed three times with 10 ml portions of water. Then, the solution was dried over anhydrous magnesium sulfate and filtered. The filtrate was admixed with 100 ml of activated carbon and was then filtered again.

The resulting filtrate was concentrated under reduced pressure to afford an oil comprising the racemic tri-N-benzyloxycarbonyl-arphamenine A compounds of the formula

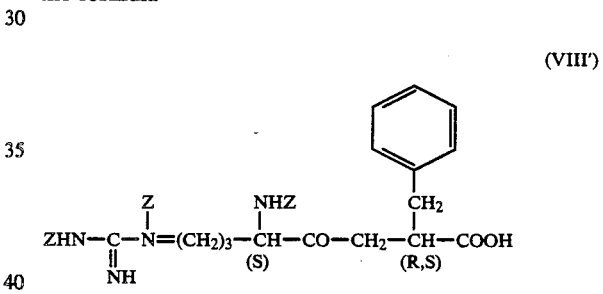

This product was dissolved in 2 ml of chloroform, and the solution was adsorbed onto a silica gel column (CC-7, a product of Mallinckrodt Inc., 35 g). The column was developed with chloroform-methanol (120:1) for chromatography, and the eluate was collected in 3.5 ml-fractions. Fractions Nos. 23 to 26 afforded 352 mg of a compound giving a spot at a high Rf value, and Fractions Nos. 39 to 42 afforded 67 mg of a compound giving a spot at a low Rf value. The remaining fractions Nos. 27 to 38 gave 212 mg of a mixture of these two compounds. Said compound having the high Rf value is designated as compound (VIIIa') of the formula

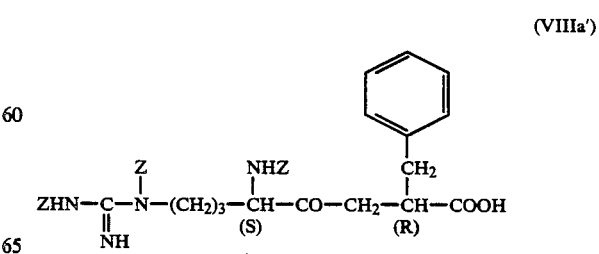

and the compound having the low Rf value is designated as compound (VIIIb') of the formula

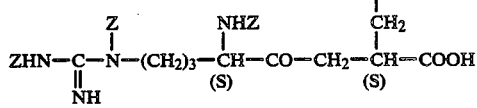 (VIIIb')

Their physical constants are shown below.

Compound (VIIIa')

$^1$H-NMR ($\delta$, 80 MHz, in CDCl$_3$): 8.26 (=NH), 7.23 (C$_6$H$_5$), 5.18, 5.11, 5.01

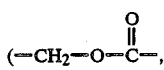

respectively), 4.63

$[\alpha]_D^{25}$ +21° (c=0.6, CHCl$_3$).

Mass spectrum (FD): m/e 724 (m+1)

A methyl ester of the compound (VIIIa') which was obtained by treating this compound (VIIIa') with diazomethane showed a mass spectrum (FD) of m/e 738 (m+1).

Compound (VIIIb')

$^1$H-NMR ($\delta$, 80 MHz, in CDCl$_3$): 9.25 (=NH), 7.31, 7.28, 7.24 (C$_6$H$_5$), 5.18, 5.08, 5.03

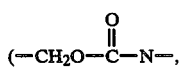

respectively), 4.55

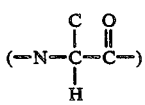

$[\alpha]_D^{25}$ +16° (c=0.4, CHCl$_3$)

A methyl ester of the compound (VIIIb') which was obtained by treating this compound (VIIIb') with diazomethane showed a mass spectrum (FD) of m/e 738 (m+1).

(c) Deprotection reaction (Formation of Arphamenine A)

100 mg of the tri-N-benzyloxycarbonyl-arphamenine A of the formula (VIIIa') and the tri-N-benzyloxycarbonyl-epi-arphamenine A of the formula (VIIIb') as obtained in the above step (b) were separately dissolved in a mixture of 3 ml of dioxane, 0.5 ml of distilled water and 0.3 ml of 1N hydrochloric acid. The resultant solution was catalytically reduced for 5 hours in an atmosphere of hydrogen at 3 atms. in the presence of 10 mg of palladium black as a catalyst, for the removal of the benzyloxycarbonyl groups. Thin-layer chromatography (Merck's silica gel plate Art 5715, developed with phenol-water (3:1)) of the reaction mixture confirmed the dis-appearance of the compound (VIIIa') or (VIIIb'), and the formation of a compound giving a spot at the same Rf value as for arphamenine A was observed. Then, the reaction mixture was filtered to remove the catalyst, and the filtrate was evaporated under reduced pressure to remove the solvent and water. The resulting crude powder of arphamenine A or epi-arphamenine A hydrochloride was dissolved in 0.1 ml of water, and the solution was adsorbed onto 4 ml of a nonionic adsorbent resin, Diaion HP-20. The resin was developed with water and the eluate was collected in 0.4 ml-fraction. The desired arphamenine A was eluted in Fractions Nos. 12 to 28. These active fractions were combined together and concentrated under reduced pressure to a volume of about 1 ml. About 0.2 ml of Dowex WGR was added to the concentrate, which was then adjusted to neutral pH and filtered. The Dowex resin was washed with water, and the washings were combined with the filtrate. The combined solution was concentrated and lyophilized to give 23 mg of the desired arphamenine A. Yield: 46.4%.

The desired arphamenine A so synthetically produced as above from said compound (VIIIa') was represented by the formula (Ia) given hereinbefore, and it showed, in thin-layer chromatography, the same Rf value as that of a naturally occurring arphamenine A which was obtained from the fermentative process. The arphamenine A as synthesized from the compound (VIIIa') is designated as Substance (I'). The corresponding substance which was synthesized similarly from the aforementioned eip-arphamenine A derivative (VIIIb') is epi-arphamenine A of the formula (Ib) given before, and it is designated as Substance (I"). The physical properties of these substances (I') and (I") are mentioned below.

Substance (I') (the 2S-isomer) (namely, arphamenine A)

$[\alpha]_D^{25}$ +23.5° (c=1.0, H$_2$O). $^1$H-NMR ($\delta$, 80 MHz, in D$_2$O): 7.80–6.98 (C$_6$H$_5$), 4.83 (CH), 3.69–3.84 (CH, CH$_2$), 3.34–3.68 (CH$_2 \times 2$), 2.30–2.70 (CH$_2$), 2.01–2.30 (CH$_2$). Mass spectrum (SIMS): m/e 321 (m+1), (DF): m/e 321 (m+1).

Sakaguchi's reaction and ninhydrin reaction: Positive, respectively.

Aminopeptidase B-inhibitory activity (IC$_{50}$): 0.007 mcg/ml. (a naturally occuring arphamenine A: 0.005 mcg/ml)

Substance (I") (the 2S-isomer) (namely, epi-arphamenine A)

$[\alpha]_D^{25}$ +19.0 (c=1.0, H$_2$O). $^1$H-NMR ($\delta$, 80 MHz, in D$_2$O): 7.78–7.86 (C$_6$H$_5$), 4.86 (CH), 3.72–3.85 (CH, CH$_2$), 3.35–3.67 (CH$_2 \times 2$), 2.35–2.70 (CH$_2$), 2.01–2.30 (CH$_2$). Mass spectrum (SIMS): m/e 321 (m+1), (FD): m/e 321 (m+1).

Sakaguchi's reaction and ninhydrin reaction: Positive, respectively.

The aminopeptidase B-inhibitory activities (IC$_{50}$) described above were determined by a modification of the method of Hoppusu disclosed in the specification of U.S. Pat. No. 4,595,698.

What we claim is:

1. A process for the production of optically active arphamenine A of the formula (Ia)

and optically active epi-arphamenine A of the formula (Ib)

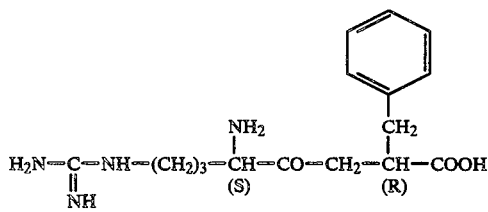

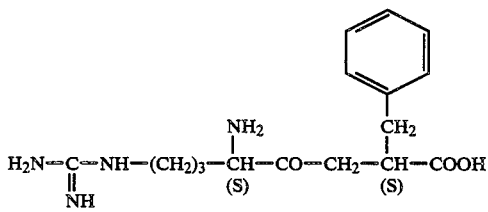

which comprises the consecutive steps of:
(i) reacting equimolar proportions of an optically active L-arginine amino-protected derivative represented by the formula (V)

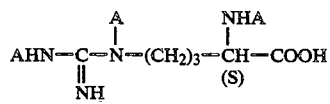

wherein A denotes an amino-protecting group selected from the group consisting of benzyloxycarbonyl, p-nitrobenzyloxycarbonyl and p-methoxybenzyloxycarbonyl, with ethyl chloroformate in an anhydrous organic solvent at a temperature of −20° C. to 0° C. and in the presence of an acid-binding agent to form the mixed acid anhydride of the formula (VI)

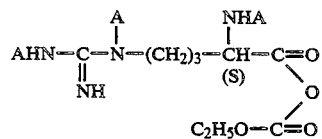

wherein A is a defined above, followed by reacting the latter reaction product of the formula (VI) with diazomethane at a temperature of from −20° C. to 10° C. to produce an optically active diazomethane derivative of the formula (VII)

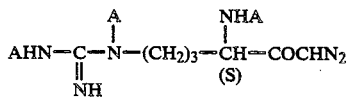

wherein A is as defined above,
(ii) reacting the diazomethane derivative of the formula (VII) with hydrobromic acid in acetic acid and diethyl either at a temperature in the range of −10° C. to 10° C. to form a bromo derivative of the formula (IIa)

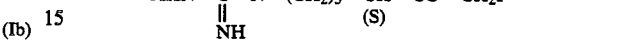

wherein A is as defined above, which is then reacted with sodium iodide in an inert solvent at room temperature to produce an iodo derivative of the formula (IIb)

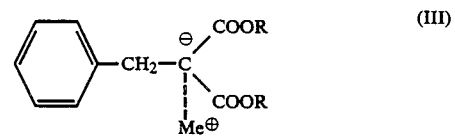

wherein A is as defined above,
(iii) condensing the resulting iodo derivative of the formula (IIb) with an alkali metal salt of a benzyl-substituted malonic acid diester of the formula (III)

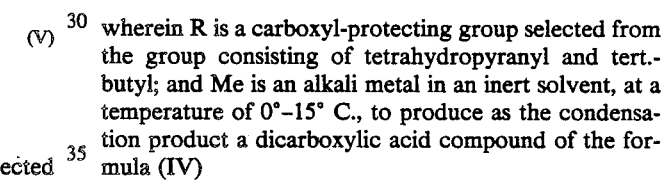

wherein R is a carboxyl-protecting group selected from the group consisting of tetrahydropyranyl and tert.-butyl; and Me is an alkali metal in an inert solvent, at a temperature of 0°–15° C., to produce as the condensation product a dicarboxylic acid compound of the formula (IV)

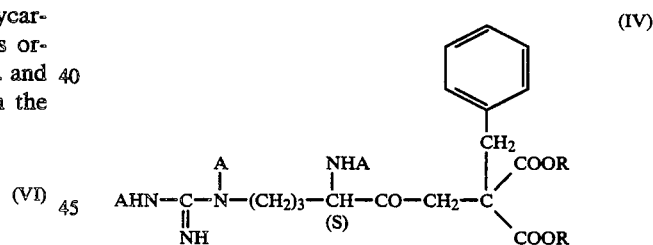

wherein A and R are each as defined above,
(iv) hydrolysing at a temperature ranging from ice-cooling to room temperature the dicarboxylic acid compound of the formula (IV) into the free dicarboxylic acid compound of the formula (IVa)

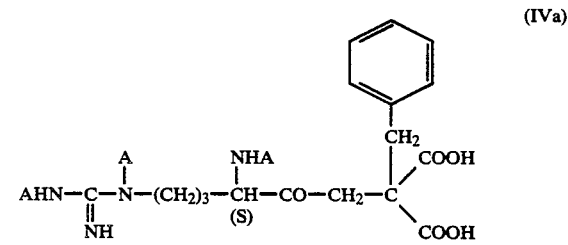

wherein A is as defined above, under such weakly acidic conditions that the asymmetric carbon atom having the S-configuration in the compound of the formula (IVa) does not undergo racemization, (v) removing one carboxyl group from the dicarboxylic acid compound (IVa) by heating the latter in an organic solvent in the presence of an alkali metal chloride at a temperature of 100°–130° C., to produce a racemic mixture of monocarboxylic acid compounds of the formula (VIII)

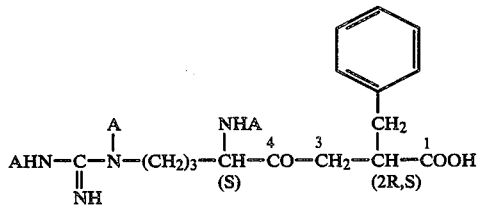

(VIII)

wherein A is as defined above, and (vi) chromatographying the racemic monocarboxylic acid compounds (VIII) into the optically active arphamenine A amino-protected derivative (2R-isomer) of the formula (VIIIa)

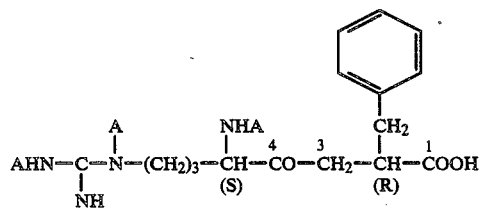

(VIIIa)

and the optically active epi-arphamenine A amino-protected derivative (2S-isomer) of the formula (VIIIb)

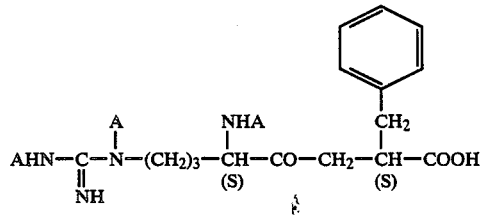

(VIIIb)

wherein A is a defined above, and (vii) removing the amino-protecting group (A) from the 2R-isomer compound of the formula (VIIIa) and from the 2S-isomer comound of the formula (VIIIb) respectively at room temperature by catalytic hydrogenolysis to produce the optically active arphamenine A (the 2R-isomer) of the formula (Ia)

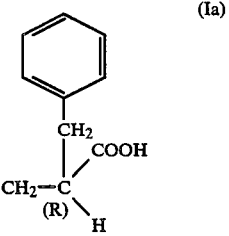

(Ia)

and the optically active epi-arphamenine A (the 2S-isomer) of the formula (Ib)

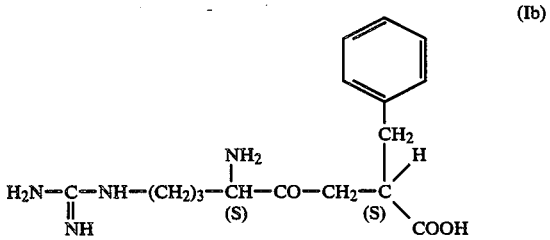

(Ib)

* * * * *